United States Patent [19]

Marsh et al.

[11] 4,080,563

[45] Mar. 21, 1978

[54] HAYLAGE/SILAGE MOISTURE TESTER

[75] Inventors: Norman F. Marsh, Auburn; Maurice J. Snell, Virden, both of Ill.

[73] Assignee: Dickey-john Corporation, Auburn, Ill.

[21] Appl. No.: 739,693

[22] Filed: Nov. 8, 1976

[51] Int. Cl.² .......................................... G01R 27/26
[52] U.S. Cl. .............................. 324/61 R; 324/61 QS
[58] Field of Search ............... 324/61 R, 61 P, 61 QS, 324/61 QL

[56] References Cited

U.S. PATENT DOCUMENTS

| | | | |
|---|---|---|---|
| 2,759,147 | 8/1956 | Stein | 324/61 R |
| 2,993,168 | 7/1961 | Burnette, Jr. | 324/61 R |
| 3,025,465 | 3/1962 | Breen | 324/61 R |
| 3,320,528 | 5/1967 | Esenwein | 324/61 R |
| 3,681,685 | 8/1972 | Tarry et al. | 324/61 QS |
| 3,739,264 | 6/1973 | Resh | 324/61 R |
| 3,794,911 | 2/1974 | Fathauer | 324/61 QS |
| 3,950,698 | 4/1976 | Wochnowski | 324/61 R |

*Primary Examiner*—Stanley T. Krawczewicz
*Attorney, Agent, or Firm*—Olson, Trexler, Wolters, Bushnell & Fosse, Ltd.

[57] ABSTRACT

A moisture tester is provided for testing a sample of feed of the silage, haylage, and like compressible variety. The tester includes a chamber for receiving a feed sample. A compressible piston compresses the feed sample in the chamber to a predetermined density to provide accurate, reliable, reproducible results. The chamber comprises spaced electrodes constituting a capacitor such that the dielectric constant of the capacitor is modified in accordance with moisture within the feed sample. A circuit functionally including the capacitor develops a signal in accordance with the moisture content of the sample. A readout, responsive to the circuit signal, provides a visual indication of the feed sample moisture content. A circuit trigger is automatically operated by the compression exerted upon the feed sample to start circuit operation and provide the feed sample moisture content readout.

15 Claims, 10 Drawing Figures

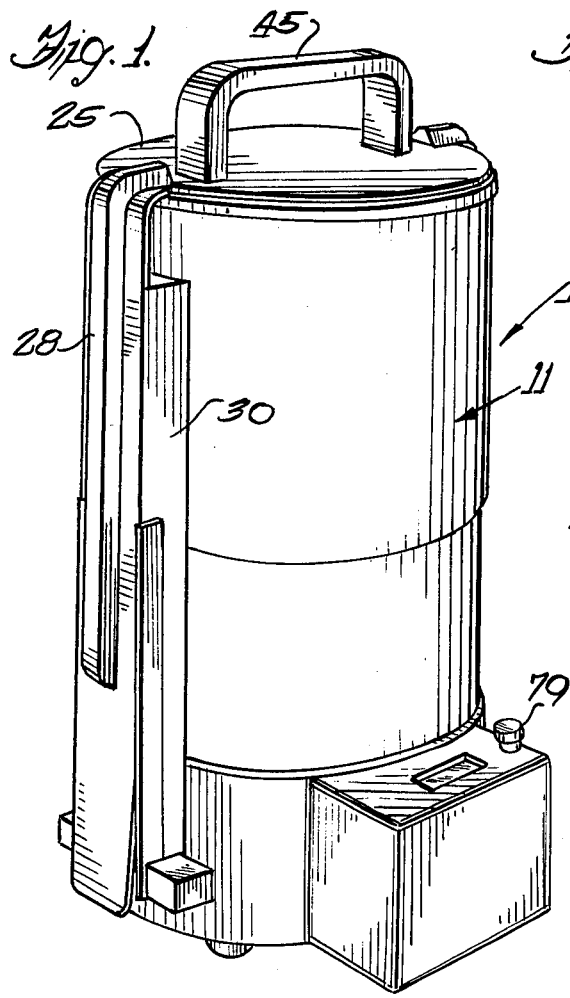
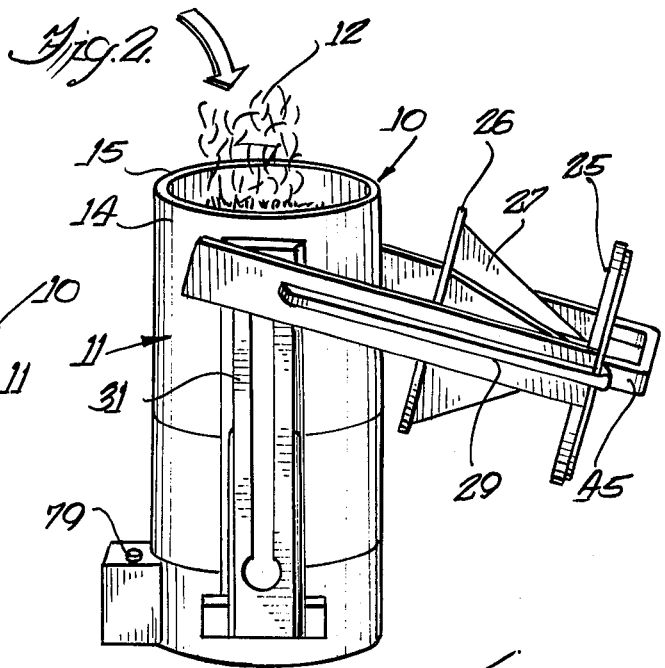
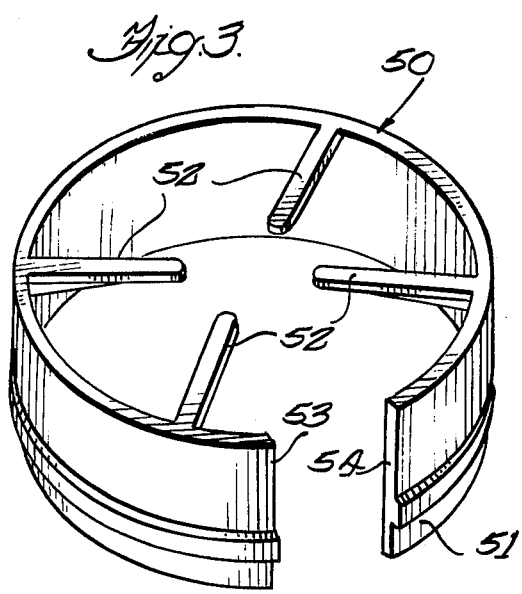
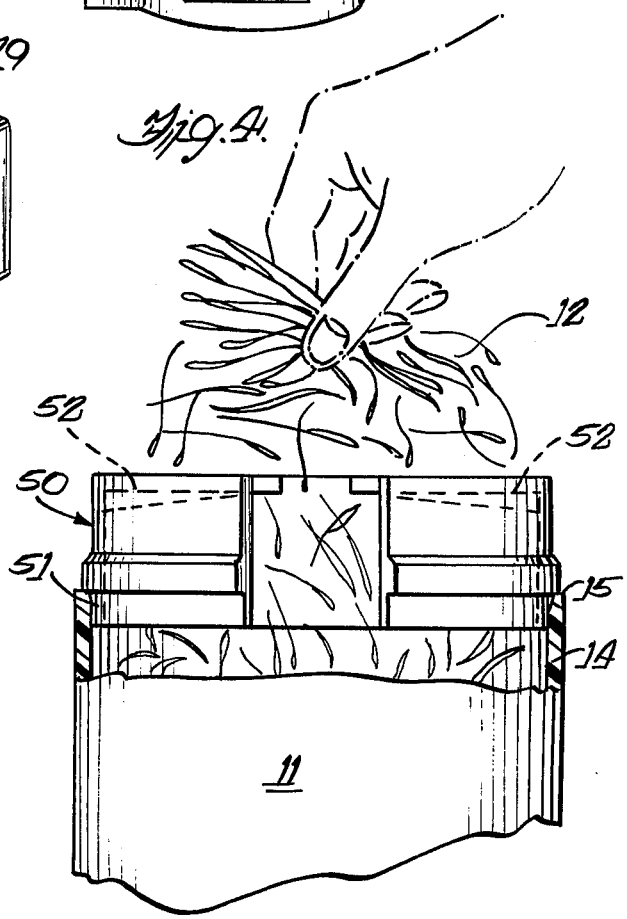

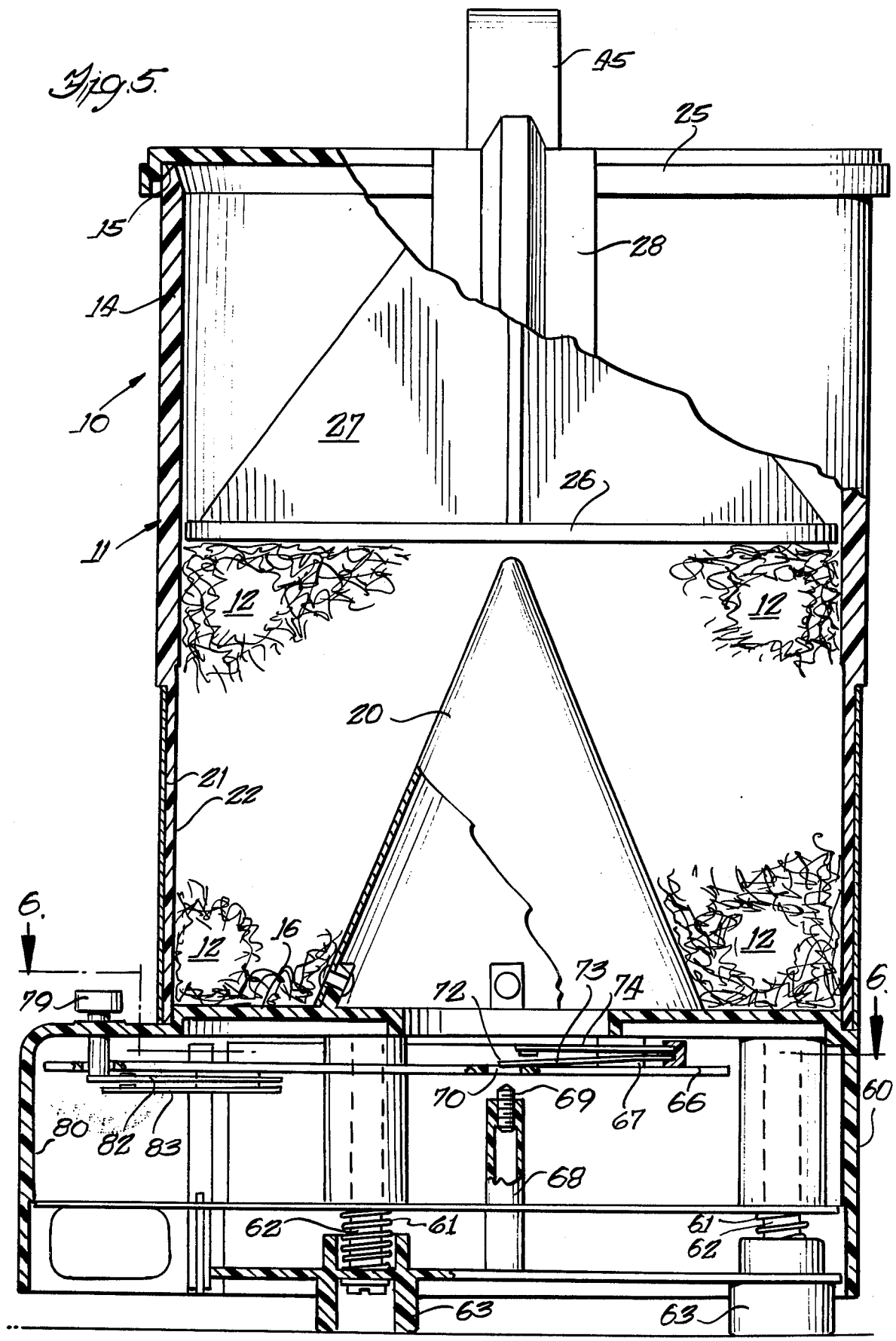

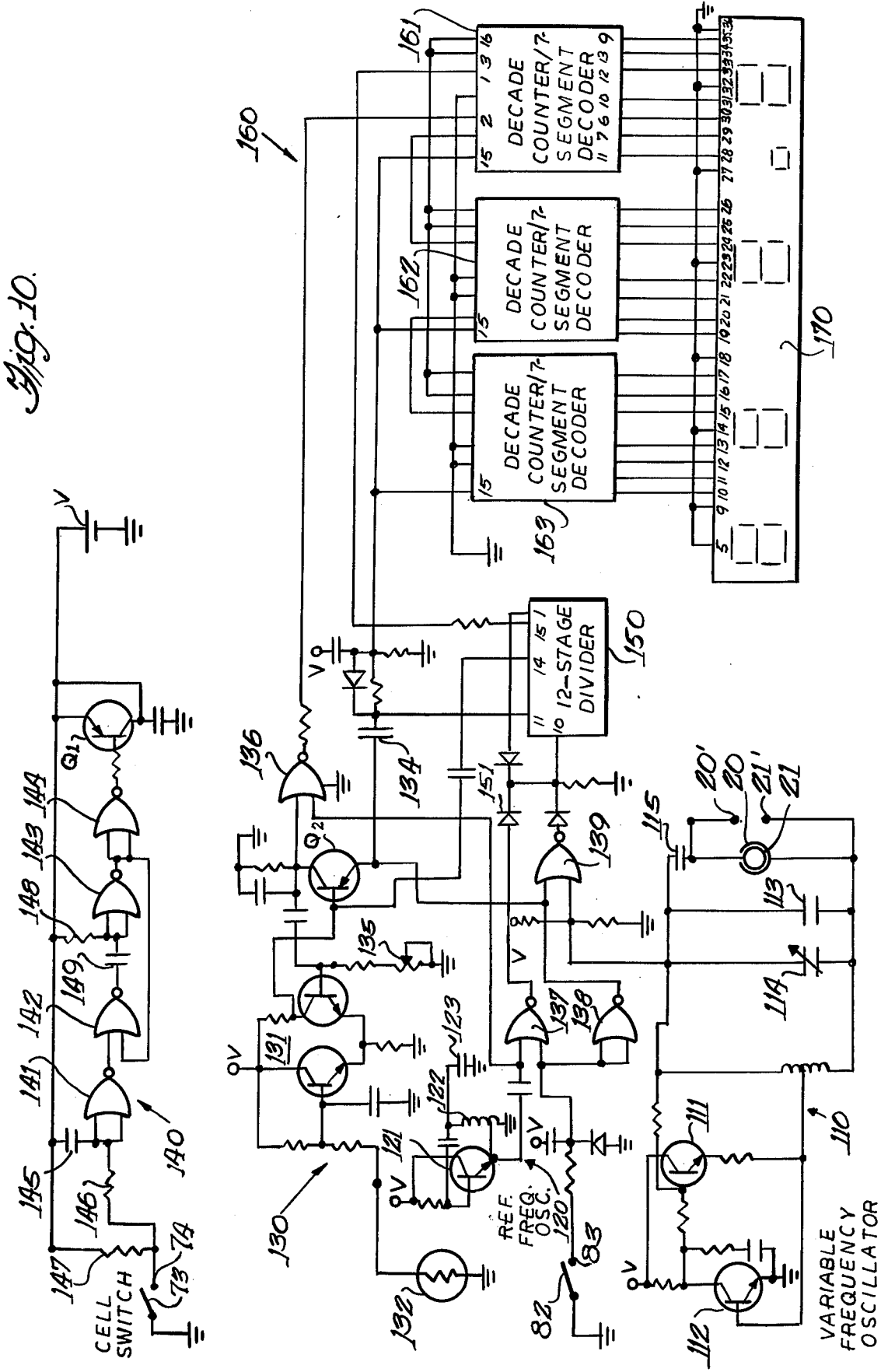

HAYLAGE/SILAGE MOISTURE TESTER

BACKGROUND OF THE INVENTION

This invention relates generally to moisture testing apparatus, and more particularly to apparatus for testing the moisture content of animal feeds such as silage, haylage and the like.

Data regarding the moisture content of animal feeds has long been important to the proper care and maintenance of agricultural animals. One such device which has met with considerable commercial success in testing the moisture content of grains and like feeds is that disclosed and claimed in U.S. Pat. No. 3,794,911.

One of the difficulties in testing animal feed of the forage variety such as haylage and silage is that these feeds are relatively compressible. When using previous electrical test apparatus with these feeds, considerably different readings can be obtained from test samples in correspondingly different states of compression.

It is accordingly the object of the present invention to provide a moisture tester for silage, haylage and other like feeds which provides reliable, reproducible data.

A more specific object is to provide a moisture tester in which the silage, haylage or like feed sample can be compressed to a predetermined extent prior to testing to give reliable, reproducible results.

Another object is to provide a moisture tester which is rugged and easy to use in operation. An associated object is to provide such a moisture tester which can be used by even inexperienced personnel. Another related object is to provide such a moisture tester which can be offered at an attractive final sales price.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 1 is a perspective view of the novel moisture tester of the present invention;

FIG. 2 is a perspective view showing the moisture tester as it appears when a feed sample is being placed in the tester;

FIG. 3 is a perspective view of a sample break-up ring associated with the tester;

FIG. 4 is an elevational view showing the moisture tester and the break-up ring as they appear when a feed sample is being loaded into the tester;

FIG. 5 is an elevational view of the moisture tester as it appears immediately prior to testing a feed sample for moisture content, portions of the tester being broken away for additional clarity of detail;

FIG. 10 is a schematic diagram of the electrical circuit used in the illustrated embodiment of the invention.

DETAILED DESCRIPTION

Figure 6:
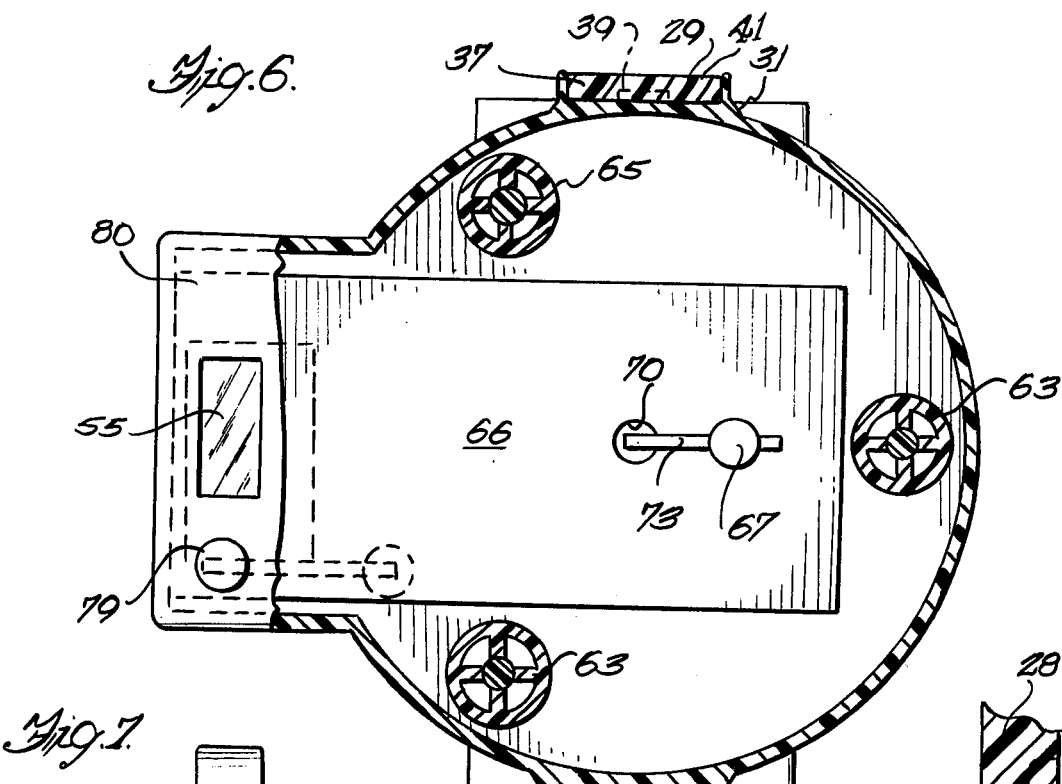
FIG. 6 is a sectional view taken substantially in the plane of lines 6—6 in FIG. 5.

While the invention will be described in connection with a preferred embodiment, it will be understood that it is not intended to limit the invention to this embodiment. On the contrary, it is intended to cover all alternatives, modifications and equivalents as may be included within the spirit and scope of the invention as defined by the appended claims.

The moisture tester 10 can be considered to include, in its general aspect, a chamber 11 adapted for receiving a quantity of forage such as haylage or silage 12 which is to be tested for moisture content. This chamber 11 here includes a right circular cylindrical outer wall 14 which terminates in an upper mouth-defining lip or edge 15, and at a lower planar disk-like bottom 16.

To test the moisture content of the haylage or silage sample 12, spaced electrodes are formed so as to constitute a capacitor of the chamber 11. The dielectric constant of the chamber-capacitor is modified in accordance with the dielectric constant of the feed sample due to moisture in the feed sample. To accomplish this, a centralized, conical metal electrode probe 20 extends from the chamber bottom 16 and forms one capacitor element. An exterior chamber metal wall 21 member forms the opposite capacitor element. The element 21 is insulated from the interior chamber by a lower portion 22 of the plastic or other insulating material forming the chamber 11.

In accordance with the invention, the feed 12 is compressed to a predetermined extent after it is deposited within the chamber 11 to provide a predetermined feed density and corresponding moisture test results of predetermined reproducibility and reliability. To this end, a cover 25 mounts a compressor piston 26 by appropriate bracing 27. The piston 26 is caused to move axially of the chamber 11 along a relatively precise path of travel by diametrically opposed slides 28 and 29 affixed to the cover 25 and adapted for engagement with slide guides 30 and 31 carried on the outside of the chamber 11. Here, pins 32 and 33 terminating in expanded retainer feet 34 and 35 fit in slots 36 and 37 to secure the slides 28 and 29 on the guides 30 and 31. Ridges 38 and 39 on the slides 28 and 29 are adapted to be urged over inclined tangs 40 and 41 on the slide guides 30 and 31 to retain the slides 28 and 29, piston 26 and cover 25 in a closed position.

It is to be noted that a predetermined axial spaced relationship is provided between the piston 26 and the latch elements or ridges 38 and 39. This relationship is such that when the chamber is properly filled with sufficient material to be tested during a testing operation as described below, the piston will compact the material to the desired density before the elements 38 and 39 snap over the tangs 40 and 41. On the other hand, if the catch elements do engage or an interlock with the tangs 40 and 41 during a testing operation, such engagement provides an indication that the chamber has not been filled with sufficient material to obtain a correct moisture measurement.

Figure 7:
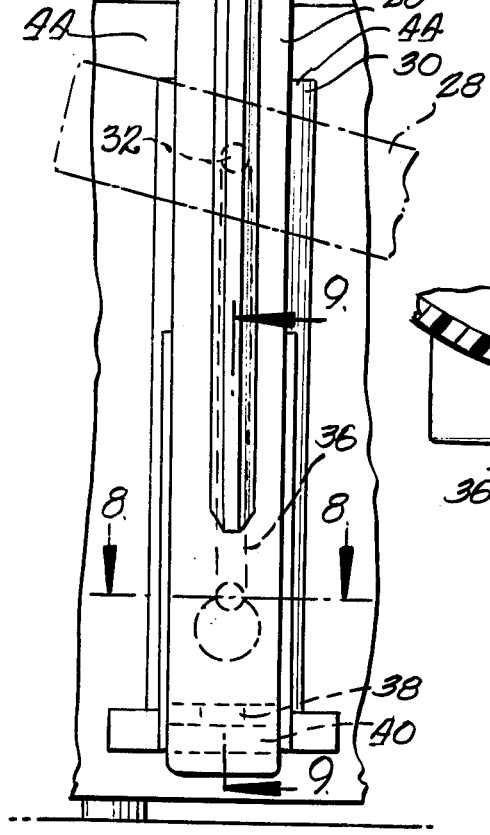
FIG. 7 is a fragmentary elevational view showing in further detail portions of the handle, cover and piston guide apparatus.
Figure 8:
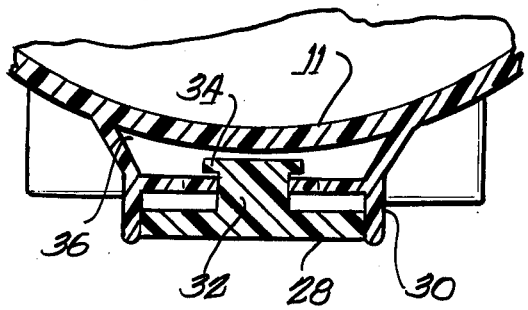
FIG. 8 is a fragmentary sectional view taken substantially in the plane of line 8—8 in FIG. 7.
Figure 9:
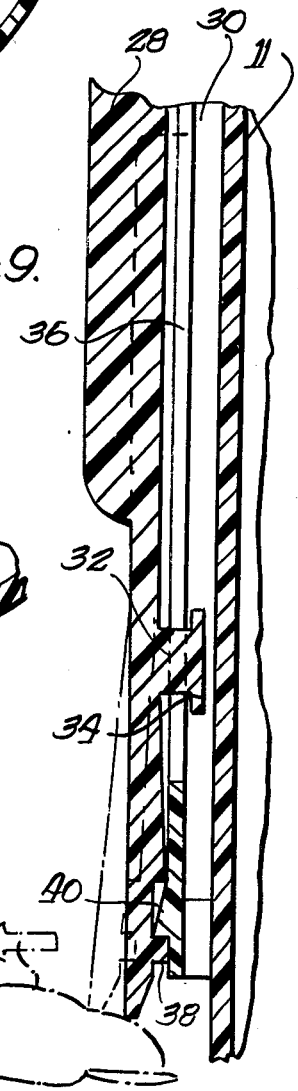
FIG. 9 is a fragmentary sectional view taken substantially in the plane of line 9—9 in FIG. 7.

Top portions 44 of the slide guides 30 and 31 are relieved to permit the cover 25 and piston 26 to be pivoted about the pins 32 and 33 out of the opening of the chamber 11 for easy test sample loading and unloading as shown in FIGS. 2 and 7. A carrying and cover-manipulating handle 45 is formed atop the cover 25.

To cause the instrument user to load silage in a uniform, preliminarily uncompacted form, a loader ring 50 can be temporarily installed atop the chamber edge 15, in a position defined by interengagement of a ring seat 51 with the chamber top 15. Inwardly projecting arms 52 break up dense clumps of test material, and encourage uniform density in the test sample. When not in use, the ring 50 can be stored within the chamber 11 by urging the ring interrupted ends 53 and 54 toward one another to permit the ring 50 to fit within the interior of the chamber 11.

It is a feature of the invention that after the feed sample has been compressed and the density of the feed within the chamber 11 has been accordingly increased to a predetermined extent, moisture testing then automatically and instantaneously occurs. To this end, the chamber 11 is mounted upon a base 60, and biasing devices urge the chamber 11 away from the base 60 under normal conditions. Here, these biasing devices take the form of coil springs 61 mounted about base pins 62. For convenience, these base pins can be secured within resilient feet 63, as illustrated in FIG. 5. It will be understood that, in the interests of unit stability, a third biasing spring, mounting pin, and foot 65 are included as suggested in FIG. 6.

After a feed sample is loaded into the chamber 11, the ring 50 is removed, the cover 25 and the piston 26 are next positioned, and the unit handle 45 is then depressed. Feed sample compression pressures rise within the cylinder 11 and pressure is exerted against the bottom of the cylinder 16 and the biasing springs 61. As the pressure exerted by the handle 45 continues to increase, the counteractive forces of these springs 61 is overcome, and the cylinder 11 is forced downwardly toward the base 60. When this occurs, an electrical circuit board 66, which is affixed to the chamber 11 (as through mount pads 67) is forced downwardly toward the base with the chamber.

Affixed to the base 60 is a finger member 68 which terminates in a threadably adjustable probe 69. As the circuit board 66 is forced downwardly toward and over the probe finger 69, the probe is inserted through an aperture 70 formed in the circuit board 66 and into engagement with the extension 72 of one of a pair of electrical contacts 73 and 74. These contacts are mounted to the circuit board 66, and are normally biased into an open condition. As the probe finger 69 engages the contact extension 72, the contact 73 is forced into a closed-circuit or "triggered" condition. At this instant, the dielectric capacitance of the chamber-capacitor 11 is measured by the circuitry and data corresponding to this capacitance or moisture content is displayed upon a readout display 55, as hereinafter described in greater detail with reference to FIG. 10. It is another feature of the invention that the finger 69 is located centrally relative to the chamber 11, the chamber bottom 16, and the central probe 20, so as to minimize indicator readout error due to chamber tilting during moisture tester operation.

If desired, the raw data or capacitance measured can be adjusted for temperature variations which would otherwise provide a false measure of the moisture content in the feed sample. To this end, a temperature compensator button 79 is mounted in a convenient place upon the display control box 80. When this compensator button 79 is depressed, contacts 82 and 83 are closed to energize temperature compensating or adjusting portions of the circuitry.

FIG. 10 shows a schematic circuit diagram of an electronic circuit which may be utilized to construct a moisture-testing apparatus in accordance with the principles of the present invention. In general, the circuit illustrated comprises a variable frequency or "test" oscillator 110, which includes a pair of oscillator transistors 111 and 112, and a fixed-frequency or "reference" oscillator 120, which included an oscillator transistor 121 and a tapped inductance coil 122. The output signal of reference oscillator 120 is applied to a three-stage counter 160. A 12-stage divider circuit 150 is responsive to the pulses generated by test oscillator 110, the forage in the test chamber, as discussed herein above. The divider circuit 150 acts as a binary counter to develop a gating pulse which is applied to counter 160 to control the length of time that the three-stage decade counter 160 counts the pulses generated by reference oscillator 120. The count thus made is visually displayed by a liquid crystal display ("LCD") 170 as a reading related to percentage by weight of the moisture content of the forage being tested. Charts or other conversion means are supplied to convert this reading to a weight-based moisture percentage figure for various types of forage.

A reading which is corrected in accordance with the temperature of the forage under test may be obtained with the temperature-correcting feature of the present invention, which includes a temperature-correcting circuit 130 with its associated actuating switch comprising a pair of contacts 82, 83 and a temperature-sensing device 132. In accordance with another feature of the present invention, a display-sustaining actuating circuit 140 may be imployed to facilitate the ease of operation of the device, as hereinafter described in greater detail.

Test oscillator 110 includes means for adjusting the "empty-chamber" frequency of the oscillator which comprises a fixed-value capacitor 113 and a variable capacitor 114, both of which are connected in parallel with a capacitance that has a value which is determined primarily by the series combination of a capacitor 115 and the coaxial capacitor formed by coaxial electrodes 20 and 21 of test chamber 11, described hereinabove. Moreover, the value of capacitor 115 could be selected to produce the desired frequency-readout characteristic (e.g., a direct readout of percent by weight of moisture content as a linear function of the changes in oscillator frequency) for the particular type of grain being tested, if desired. A pair of terminals 20' and 21' may also be provided as shown in FIG. 10 so that an additional capacitance may be conveniently placed in parallel with the capacitance formed by coaxial electrodes 20 and 21 to alter the frequency readout characteristic of the device. Variable capacitor 114 of test oscillator 110 is adjusted initially at the factory with test chamber 11 being empty so that the frequency of variable frequency oscillator 110 may be calibrated to a standard frequency which has a predetermined relationship with respect to the reference frequency. The output signal of test oscillator 110 is applied to the input 12-stage divider 150 by means of a NOR gate 139 of temperature-compensating circuit 130, as described hereinafter in greater detail.

Reference frequency oscillator 120 is adjusted at the factory to oscillate at a fixed frequency of, for example, 2.0 MHz by means of a tapped coil 122 and parallel capacitor 123 connected as shown in FIG. 10. The output signal of reference oscillator 120 is applied to three-stage decade counter 160 by means of a NOR gate 136 of temperature-compensating circuit 130, as explained hereinbelow in greater detail.

As hereinbefore set forth, divider circuit 150 divides or "counts down" the frequency of the output signal from test oscillator 110 to develop a gating pulse which controls the counting time of three-stage decade counter 160. Although any suitable 12-stage divider may be utilized for divider 150, a well-known integrated circuit made by National Semiconductor Corporation, for example, and known as a "CD4020, 14-stage ripple-carry binary counter-divider" has been found particularly well adapted for use in the illustrated embodiment of the invention. With this circuit, input pulses from test frequency oscillator 110 are applied to the input terminal 10 of divider 150, and the output pulses of the 11th stage ($Q_{11}$) are available at an output terminal 15 of divider 150 for application to the "clock" terminal 1 of the righthand stage of counter 160 in FIG. 4, which corresponds to the least significant digit (here the tenths digit). The output of the 12th stage ($Q_{12}$) of divider 150 is returned to input terminal 10 to lock or "clamp" divider 150 to thus terminate the count. Thus, one output pulse at output terminal 15 is produced for each $2^{10}$ input pulses (i.e., 1024 pulses) applied to input terminal 15, and the duration of this pulse is the length of time it takes for the test oscillator to generate an additional $2^{10}$ pulses. Consequently, the higher the frequency of the test oscillator, the lower or shorter is the duration of the control pulse from divider 150, and vice versa.

The three-stage decade counter 160 shown in the embodiment of the invention illustrated in FIG. 10 comprises three decade counter-decoders (seven-segment) 161, 162, and 163 which directly drive a modular four-digit liquid crystal display (LCD) unit 170 of the conventional type. In this embodiment, only the three right-most digits are used, and the left-most digit is blanked out by restricting the opening of the display viewing window.

Operation of the circuit of FIG. 10 is initiated by circuit 140 by closing the "cell" switch comprising contacts 73, 74 discussed hereinabove. Actuating or "turn-on" circuitry 140 comprises four NOR gates 141–144, preferably of the conventional complementary metal oxide semiconductors "CMOS" — type such as a "CD4001, quadruple two-input NOR gate" manufactured by National Semiconductor Corporation, for example, which has a very high input impedance and high noise immunity. These gates 141–144 are connected as shown in FIG. 10 to provide an energizing or actuating cycle of a predetermined length of time (e.g., 60 seconds). This actuating cycle is made independent of other switching operations in order to sustain the display of LCD display 170 for sufficient time to enable the operator of the device to easily observe and record the reading. When the cell switch is closed, the input or NOR gate 141 is pulled low after a time delay which is provided by a capacitor 145 and a resistor 146. Resistor 147 provides a discharge path for capacitor 145 after the cell switch contacts 73, 74 open. After this delay period has been completed, and the input or NOR gate 141 goes low, the output of NOR gate 141 goes high causing the output of NOR gate 142 to go low. When the output of NOR gate 142 goes low, it immediately causes the input of NOR gate 143 to go low and stay low for a period of time determined by the RC combination resistor 148 and capacitor 149. The output of NOR gate 143 remains high as long as its input is low and this output is fed back to the input of NOR gate 143, forcing the output of gate 142 to stay low. This continues until capacitor 149 becomes charged and the input of NOR gate 143 goes high. For the period of time that the output of NOR gate 143 is high, it causes the output of NOR gate 144 to be low, thus allowing base current to flow through switching transistor $Q_1$ to turn on transistor $Q_1$ and thus supply voltage from a battery suitably mounted within the base 60 or other power supply V to the rest of the circuitry (as indicated by V at various locations in the circuit of FIG. 4). Thus, the user can create pressure on the chamber bottom 16 as described above until the reading appears and then the reading will sustain itself for a period of time such as 60 to 90 seconds, for example.

In accordance with another aspect of the embodiment of the invention illustrated in FIG. 10, a temperature-correcting circuit 130 is provided which includes a pair of switch contacts 82, 83 which are actuated by temperature-compensating button 79 hereinabove described with reference to FIG. 5. Temperature-compensating circuit 130 further includes a temperature-sensing device in the form of a thermistor 132 which is coupled to one input of a differential amplifier circuit 131. The other input of differential amplifier circuit 131 has coupled to it a potentiometer 135 (connected as a variable resistor) for enabling calibration of temperature compensation circuit 130. Differential amplifier circuit 135 may comprise a conventional integrated circuit of the type manufactured by Fairchild Semiconductor and identified as a "CD3086."

When temperature compensation button 79 is pushed, it causes both inputs of NOR gate 138 and one input of NOR gate 137 to go low. This causes the output of NOR gate 138 to go high which inhibits NOR gate 139 from transmitting any further pulses from test oscillator 110 to divider 150. The output of NOR gate 138 also provides a reset pulse to the divider 150 via capacitor 134 at the instant that NOR gate 138 goes high. This high signal from NOR gate 138 also enables a temperature-compensation "one-shot" circuit by providing drive current to switching transistor $Q_2$. NOR gate 137 transmits the reference oscillator output signal to the clock input of divider 150 via diode 151 and, when Q11 (terminal 15) of divider 150 goes high, it enables counter stage 161 to begin counting by raising the clock input to a high state. At this same instant, Q10 (terminal 14) of divider 150 goes low and triggers the temperature "one-shot" circuit causing one input of NOR gate 136 to go high for a period of time determined by the thermistor which is connected to the temperature one-shot. For the period of time during which one input of NOR gate 136 is held high, no pulses from the reference oscillator will be transmitted through NOR gate 136 to divider 150. 1024 pulses are counted by counter 160 if there is no signal generated by the temperature correction one-shot, and this causes the final, corrected moisture reading to be 2.4% higher in the particular embodiment of the invention illustrated in FIG. 10. For example, at 25° Centigrade (77° Fahrenheit) potentiometer 135 is set to give an output pulse from the one-shot that is approximately 12 microseconds in length so that a total of 24 pulses from the reference oscillator are inhibited from being counted by counter 150, thereby yielding a count of 1000 which does not cause any change in the moisture reading. When the temperature of the grain is greater than 25° Centigrade, in this example, the output pulse of the one-shot is longer and causes counter 160 to count less than 1000 pulses, thereby causing the temperature corrected reading to be lower than the uncorrected reading.

The invention is claimed as follows:

1. A moisture tester for testing a sample of feed of the silage, haylage and like variety, comprising a chamber member for receiving the feed sample and having spaced electrodes constituting a capacitor such that the dielectric constant of the capacitor is modified in accordance with the dielectric constant of the feed sample moisture content, circuit means including said capacitor for developing a signal in accordance with the capacitor dielectric constant, indicator means responsive to said signal for providing an indication representative of said moisture content, compressor piston means adapted to slidably fit within the chamber for compressing the feed sample to a predetermined density for testing, cover means mounting the piston, a number of slides attached to the cover, and a corresponding number of slide guides carried exteriorly of the chamber member for engaging the slides and causing the slide, the cover and the piston to move along respectively predetermined paths relative to the chamber member, and circuit trigger means operable by compression exerted upon the feed sample for triggering operation of the circuit means to provide an instantaneous indication of the feed sample moisture content.

2. A moisture tester according to claim 1 wherein said chamber member is at least partially defined by a bottom, and wherein said trigger means are located centrally of said bottom to minimize moisture indicator read-out error due to chamber tilting during the moisture tester operation.

3. A moisture tester according to claim 1 including a base member carrying said chamber member for limited motion toward and away from the base member, and biasing means urging the chamber member away from the base member.

4. A moisture tester according to claim 3 including trigger means comprising finger means mounted on one of said chamber and base members, and first and second trigger contacts mounted on the other of said base and chamber members and biased into a contact-open position relative to one another, the finger means being located to engage one of said contacts and urge it against the other contact into a contact-closed position as the chamber member is urged toward the base member.

5. A moisture tester for testing a sample of feed of the silage, haylage and like variety, comprising a chamber member partly defined by a chamber top, the chamber being adapted for receiving the feed sample and having spaced electrodes constituting a capacitor such that the dielectric constant of the capacitor is modified in accordance with the dielectric constant of the feed sample due to feed sample moisture content, circuit means including said capacitor for developing a signal in accordance with the moisture content of the sample and for providing an indication representative of the moisture content, compressor piston means adapted to slidably fit within the chamber for compressing the feed sample to a predetermined density for testing, cover means mounting the piston, a number of slides extending from the cover, and a corresponding number of slide guides carried exteriorly of the chamber member for engaging the slides and causing the slide, the cover and the piston to move along respectively predetermined paths relative to the chamber member, a base member carrying the chamber member for a limited motion toward and away from the base member, trigger means including finger means mounted on one of said chamber and base members, and first and second trigger contacts mounted on the other of the base and chamber members and biased into a contact open position relative to one another, the finger means being located to engage one of the contacts and urge that contact against the other contact into a contact-closed position as the chamber member is urged toward the base member to provide an instantaneous indication representative of the feed sample moisture content when the feed sample is compressed to a predetermined degree.

6. A moisture tester according to claim 5 wherein said chamber member is at least partially defined by a bottom, and wherein said trigger means are located centrally of the bottom to minimize moisture indicator read-out error due to chamber tilting during the moisture tester operation.

7. A moisture tester according to claim 5 including guide pin means permitting the cover, piston and slides to be pivoted away from the chamber top.

8. A moisture tester for testing a sample of feed of the silage, haylage and like variety, comprising a chamber member having a top, being adapted for receiving the feed sample and having spaced electrodes constituting a capacitor such that the dielectric constant of the capacitor is modified in accordance with the dielectric constant of the feed sample moisture content, circuit means including said capacitor for developing a signal in accordance with the capacitor dielectric constant, indicator means responsive to said signal for providing an indication representative of said moisture content, compressor piston means adapted to slidably fit within the chamber for compressing the feed sample to a predetermined density for testing, cover means mounting the piston, a number of slides attached to the cover, and a corresponding number of slide guides carried exteriorly of the chamber member for engaging the slides and causing the slide, the cover and the piston to move along respectively predetermined paths relative to the chamber member.

9. A moisture tester according to claim 8 including handle means mounted upon the cover means and adapted for carrying the moisture tester.

10. A moisture tester according to claim 9 including latch means for latching the cover means in a closed position over the chamber mouth.

11. A moisture tester according to claim 8 including guide pin means permitting the compressor means and slides to be pivoted away from the chamber top.

12. A moisture tester according to claim 11 including latch means on the guide pin means for latching the cover means in a closed position over the chamber top.

13. A moisture tester according to claim 8, wherein said tester means includes a handle means connected with said piston selectively for depressing the piston to compress the feed and for carrying the tester, first and second releasably cooperable latch elements respectively interconnected with and movable with said handle means and fixed on said chamber member, said latch elements being located with respect to said piston for latching the handle means in a tester carrying position and also for indicating, upon latch engagement, that there is insufficient feed in the chamber for testing.

14. A moisture tester for testing a sample of feed of the silage, haylage and like variety, comprising a chamber member at least partly defined by a bottom and being adapted for receiving the feed sample and having spaced electrodes constituting a capacitor such that the dielectric constant of the capacitor is modified in accordance with the dielectric constant of the feed sample moisture content, conical probe means affixed at the center of the chamber for distributing the feed sample material in a uniform density throughout the chamber, circuit means including said capacitor for developing a signal in accordance with the capacitor dielectric constant, indicator means responsive to said signal for providing an indication representative of said moisture content, compressor means acting with the chamber member and probe means for compressing the feed sample to a predetermined density of uniform value throughout the feed sample for testing, and circuit trigger means operable by compession exerted upon the feed sample for triggering operation of the circuit means to provide an instantaneous indication of the feed sample moisture content and being located centrally of the chamber bottom to minimize moisture indicator read-out error due to chamber tilting during the moisture tester operation.

15. A moisture tester for testing a sample of feed of the silage, haylage and like variety, comprising a chamber member having a bottom and being adapted for receiving the feed sample and having spaced electrodes constituting a capacitor such that the dielectric constant of the capacitor is modified in accordance with the dielectric constant of the feed sample due to feed sample moisture content, a conical probe affixed to the chamber bottom for uniformly distributing the feed sample material throughout the chamber, circuit means including said capacitor for developing a signal in accordance with the moisture content of the sample and for providing an indication representative of the moisture content, compressor means for compressing the uniformly distributed feed sample to a predetermined uniform density for testing, a base member carrying the chamber member for a limited motion toward and away from the base member, trigger means located centrally of the chamber bottom and including finger means mounted on one of said chamber and base members, and first and second trigger contacts mounted on the other of the base and chamber members and biased into a contact open position relative to one another, the finger means being located to engage one of the contacts and urge that contact against the other contact into a contact-closed position as the chamber member is urged toward the base member to provide an instantaneous indication representative of the feed sample moisture content when the feed sample is compressed to a predetermined degree.

* * * * *